(12) United States Patent
Ryu, Sr. et al.

(10) Patent No.: US 11,185,300 B2
(45) Date of Patent: Nov. 30, 2021

(54) DUAL EXPOSURE BUTTONS CONTROLLED BY A SWITCH OR AN AUDIO GUIDE

(71) Applicants: Seung Bum Ryu, Sr., Irving, TX (US); Kun Sang Ryu, Bu (KR); Duck Chul Min, Se (KR); Kwang Ho Ryu, Ya (KR)

(72) Inventors: Seung Bum Ryu, Sr., Irving, TX (US); Kun Sang Ryu, Bu (KR); Duck Chul Min, Se (KR); Kwang Ho Ryu, Ya (KR)

(*) Notice: Subject to any disclaimer, the term of this patent is extended or adjusted under 35 U.S.C. 154(b) by 336 days.

(21) Appl. No.: 15/694,777

(22) Filed: Sep. 2, 2017

(65) Prior Publication Data

US 2019/0069863 A1  Mar. 7, 2019

(51) Int. Cl.
*A61B 6/00* (2006.01)
*A61B 6/14* (2006.01)
*A61B 6/10* (2006.01)

(52) U.S. Cl.
CPC .............. *A61B 6/467* (2013.01); *A61B 6/107* (2013.01); *A61B 6/14* (2013.01); *A61B 6/4405* (2013.01); *A61B 6/463* (2013.01); *A61B 6/483* (2013.01); *A61B 6/54* (2013.01); *A61B 6/56* (2013.01); *A61B 6/461* (2013.01)

(58) Field of Classification Search
CPC ......... A61B 6/107; A61B 6/14; A61B 6/4405; A61B 6/461; A61B 6/463; A61B 6/467; A61B 6/483; A61B 6/54; A61B 6/56
See application file for complete search history.

(56) References Cited

U.S. PATENT DOCUMENTS

| | | | |
|---|---|---|---|
| 2010/0104066 A1* | 4/2010 | Foos | A61B 6/4405 378/62 |
| 2016/0081642 A1* | 3/2016 | Okusu | G06F 3/04845 378/62 |
| 2016/0361037 A1* | 12/2016 | Im | A61B 6/5217 |
| 2016/0374641 A1* | 12/2016 | Ancar | A61B 6/587 378/206 |

\* cited by examiner

*Primary Examiner* — Mark R Gaworecki

(57) ABSTRACT

A portable x-ray device for producing x-rays may include a housing; an exposure device enclosed by the housing to generate x-rays; a slide switch connected to the exposure device being movable between a first position and a second position; a first trigger to activate the exposure device when the slide switch is in the first position being positioned on a first side of the housing; a second trigger to activate the exposure device when the slide switch is in the second position being positioned on a second opposed side of the housing.

7 Claims, 15 Drawing Sheets

DUAL EXPOSURE BUTTONS CONTROLLED BY A SWITCH OR AN AUDIO GUIDE

FIELD OF THE INVENTION

The invention relates generally to medical imaging and in particular to portable X-ray imaging systems with dual exposure buttons.

BACKGROUND

Typical x-ray tubes and x-ray devices (device containing x-ray tubes) have been known and used for some time. Unfortunately, they are usually bulky and are powered by heavy, high-voltage power supplies that restrict mobility. As well, they are often difficult and time-consuming to use. In many instances, a sample for analysis must be sent to an off-site laboratory for analysis by the x-ray device.

In a typical workflow for portable radiography, a technologist is provided with a hard-copy worklist that indicates imaging requirements for various patients in the ICU. The technologist captures the images of all patients on the worklist, then at some convenient opportunity (usually after completing the rounds), downloads the captured images to a PACS (Picture Archive Communications System) for subsequent clinical and diagnostic interpretation. Unfortunately, this conventional workflow pattern can sometimes be poorly suited to the requirements of patient care. The need to upload image data to the PACS or other archive system means that interpretation of the obtained images cannot be performed on-site, but requires coordination with off-site diagnosticians. Urgent care situations require personal intervention and are handled as exceptions rather than accommodated in the workflow. It can be difficult for the clinical staff to determine the status of a worklist request until some time after the image is obtained. There can be an undesirable delay in obtaining response information for problems of tube and line placement. Significant information that can help to guide the imaging process is not made available to the technologist unless it is provided in the worklist data. In addition, quality control (QC) suffers, since the technologist must wait for off-site processing and response in order to determine whether or not an obtained image is usable for diagnostic purposes.

SUMMARY

A portable x-ray device for producing x-rays may include a housing; an exposure device enclosed by the housing to generate x-rays; a slide switch connected to the exposure device being movable between a first position and a second position; a first trigger to activate the exposure device when the slide switch is in the first position being positioned on a first side of the housing; a second trigger to activate the exposure device when the slide switch is in the second position being positioned on a second opposed side of the housing.

The x-ray device may include a function button to control the function of the x-ray device.

The x-ray device may include a display screen to display information concerning the exposure.

The x-ray device may include a controller to control the display screen.

The x-ray device may include a sensing circuit.

The x-ray device may include shielding to shield the operator of the x-ray device.

The x-ray device may include a power supply.

A portable x-ray device for producing x-rays, may include a housing; an exposure device enclosed by the housing to generate x-rays; a touch interface responsive to a touch of the user; and a voice circuit responsive to the touch interface to generate audio in response to the touch of the user.

The voice circuit may include a speaker.

The voice circuit may include a memory

BRIEF DESCRIPTION OF THE DRAWINGS

The invention may be understood by reference to the following description taken in conjunction with the accompanying drawings, in which, like reference numerals identify like elements, and in which.

DETAILED DESCRIPTION

Figure 1:
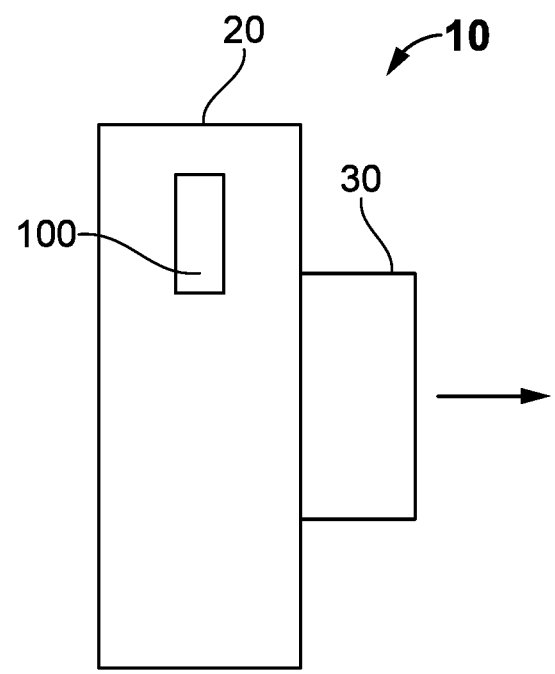
FIG. 1 illustrates a first side view of the x-ray device of the present invention.
Figure 2:
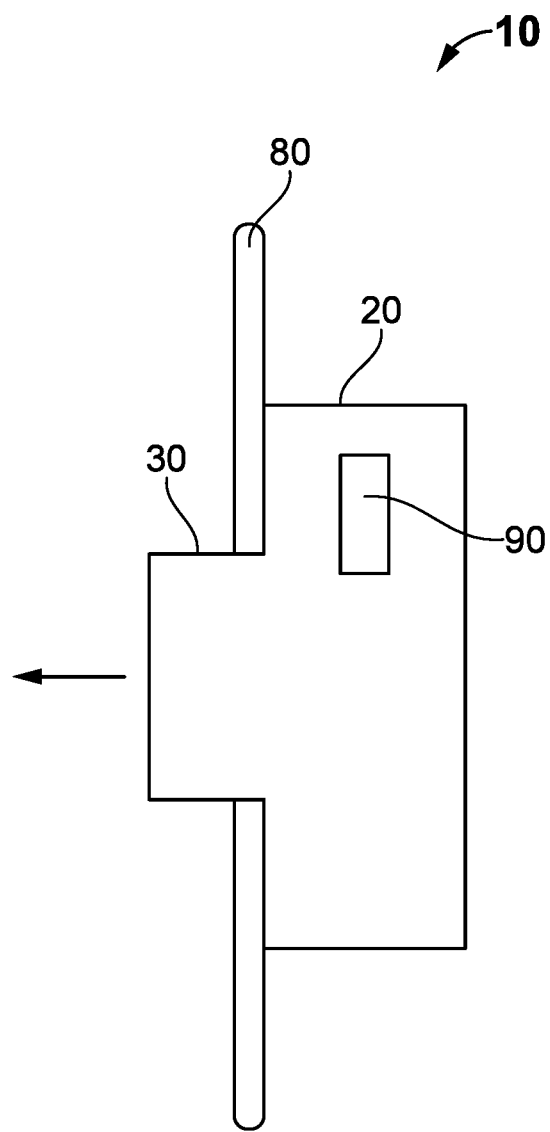
FIG. 2 illustrates a second side view of the x-ray device of the present invention.
Figure 3:
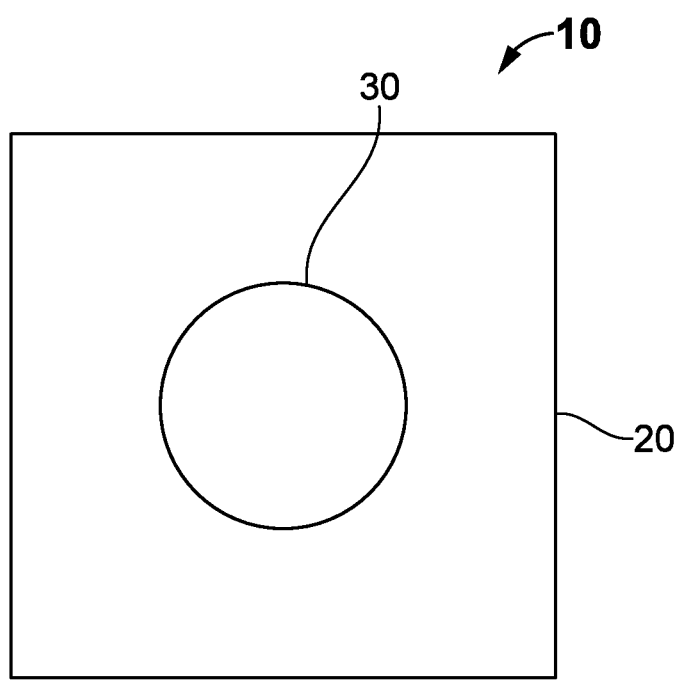
FIG. 3 illustrates a front view of the x-ray device of the present invention.
Figure 4:
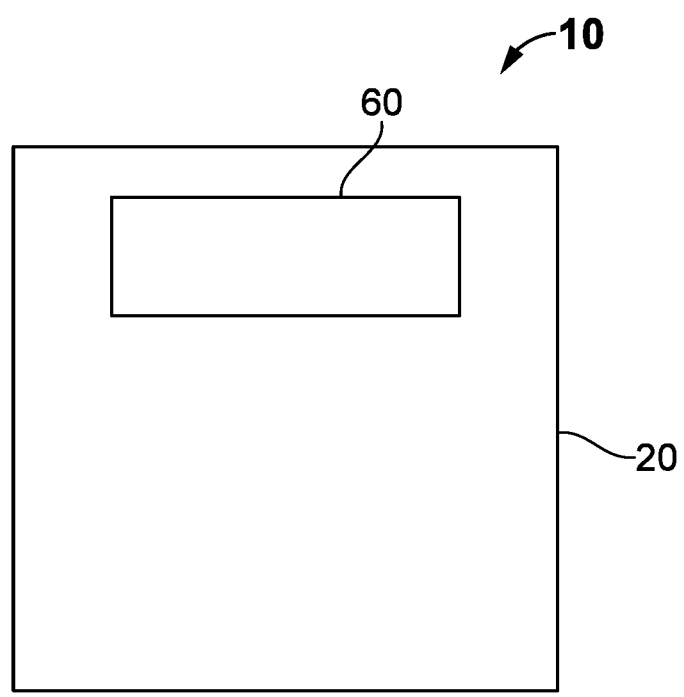
FIG. 4 illustrates a back view of the x-ray device of the present invention.
Figure 5:
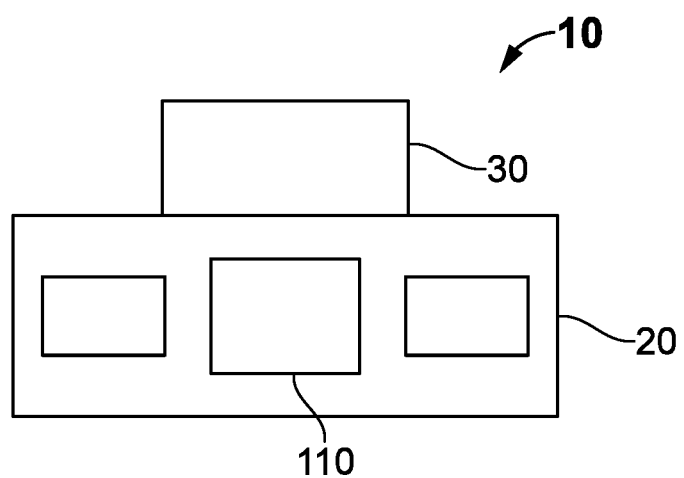
FIG. 5 illustrates a top view of the x-ray device of the present invention.
Figure 6:
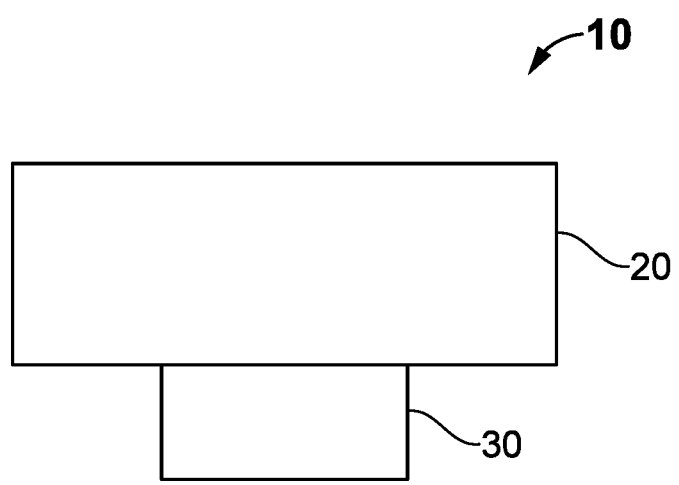
FIG. 6 illustrates a bottom view of the x-ray device of the present invention.

The present invention provides convenience to users and provides a dual exposure button controlled by a simple switch for left hand or right hand use so that people may hold and shoot with one hand.

The present invention provides an audio guide two give the user more alert and instant guide for safe usage.

As shown in FIGS. 1-6, the portable x-ray device 10 of the invention includes a housing or chassis 20 to include all the internal components of the device. The housing 20 encloses an x-ray tube 30 for producing the x-rays. The x-ray device 10 includes a power system to provide power for the device 10 and a device for sensing the x-rays, such as film, CCD sensors, or imaging plates (not shown). The x-ray device 10 also includes a device for displaying the results of the analysis such as an integrated image display screen 60; a control device such as controller 70; and radiation shielding 80 to shield the operator of the device from backscattered radiation from the sample. The x-ray device 10 also contains any other components known in the art for efficient operation (such as an x-ray collimator), including those components.

The power system of the x-ray device comprises a power source power supply, and a conversion device. The power source used in the x-ray device 10 of the invention can be any known in the art that can supply the desired amount of power, yet fit within the space limitations of the x-ray device 10.

The x-ray device of the invention also includes a control device for operating the x-ray device. Any controls known in the art can be used in the control device of the invention. Examples of such controls include up and down arrow first and second switches describe below as the first trigger 90 and the second trigger 100 with an LED readout on the display screen 60 to adjust exposure time. Indicators on the display screen 60 can include "power on," "start," and "x-rays on" LEDs. In the aspect of the invention, the control device (controller 70) is integrated into the housing 20 of the device. In another aspect of the invention, the control device may be external to the device and may be connected to remainder of the device using any known electronic connection, such as a cable. In either instance, the control device also includes a first trigger 90 and a second trigger 100 positioned on opposing sides of the housing 20 used by the operator to begin (and conclude) the x-ray exposure.

A slide switch 110 or any type of switch may be positioned on the top surface of the housing 202 select either the first trigger 904 alternatively the second trigger 100 to activate the x-ray device to expose the target object such as a tooth of the x-ray device 10 to x-rays. It is known that some people are right-handed while others are left-handed. These users who are right-handed prefer to operate the first trigger 90 which may be positioned on the right side of the housing 20. Likewise, users who are left-handed prefer to operate the second trigger 100 which may be positioned on the left side of the housing 20. The slide switch 100 allows the user to choose the most convenient trigger 90, 100.

The invention also contains a sensing circuit for sensing the x-rays reflected back from the target object. Any sensing circuit known in the art that is sensitive to x-ray radiation can be used in the invention. Examples of such sensing circuit includes x-rays receptors, x-ray film, CCD sensors, CMOS sensors, TFT sensors, imaging plates, and image intensifiers. In one aspect of the invention, a CCD sensor is used as the sensing circuit in the x-ray devices of the invention.

The x-ray device may also contain a display screen 60 for displaying the x-rays detected by the detecting means. Any display device that displays the detected x-rays in a manner that can be understood by the operator of the device can be used for the invention. Examples of displaying devices that can be used include film, imaging plates, and digital image displays such as cathode ray tubes (CRT) or liquid crystal display (LCD) screens. In one aspect of the invention, the display device can be used as a densitometer for the x-ray absorption In one aspect of the invention, the display screen 60 is integrated into the housing of the x-ray device. Such integration, however, will limit the size of the display screen 60 since too large a display spring 60 will detract from the portability of the device. In this aspect of the invention, any small display screen 60 with sufficient resolution can be used in the invention, including liquid crystal display (LCD) screen 60

In one aspect of the invention, the x-ray device 10 can contain both an integrated sensing device (such as a CCD sensor) and an integrated display screen (such as the LCD screen 60) to minimize the size and optimize the portability of the x-ray device. These two components can be used to temporarily store images in the x-ray device. Once the storage capacity for these temporary images has been reached, an optional wired or wireless connection can then provide seamless update to an external electronic system, such as a permanent database or a personal computer as known in the art. The wired or wireless connection can be made as known in the art. In one aspect of the invention, this connection is wireless since it provides true portability and freedom from line voltage.

During exposure after pressing the trigger 90, 100, x-rays are emitted from the x-ray tube 30 and strike the target object being analyzed, i.e., the teeth of a patient when the x-ray device is being used for dental purposes. To meet x-ray equipment standards, the button or trigger 90, 100 may be held down during the full length of the exposure. During exposure, the x-rays are used for analysis of the object as known in the art by using the sensing device. The operator can then view the results of the analysis in the display means and optionally download the images to an external storage device.

Figure 7:
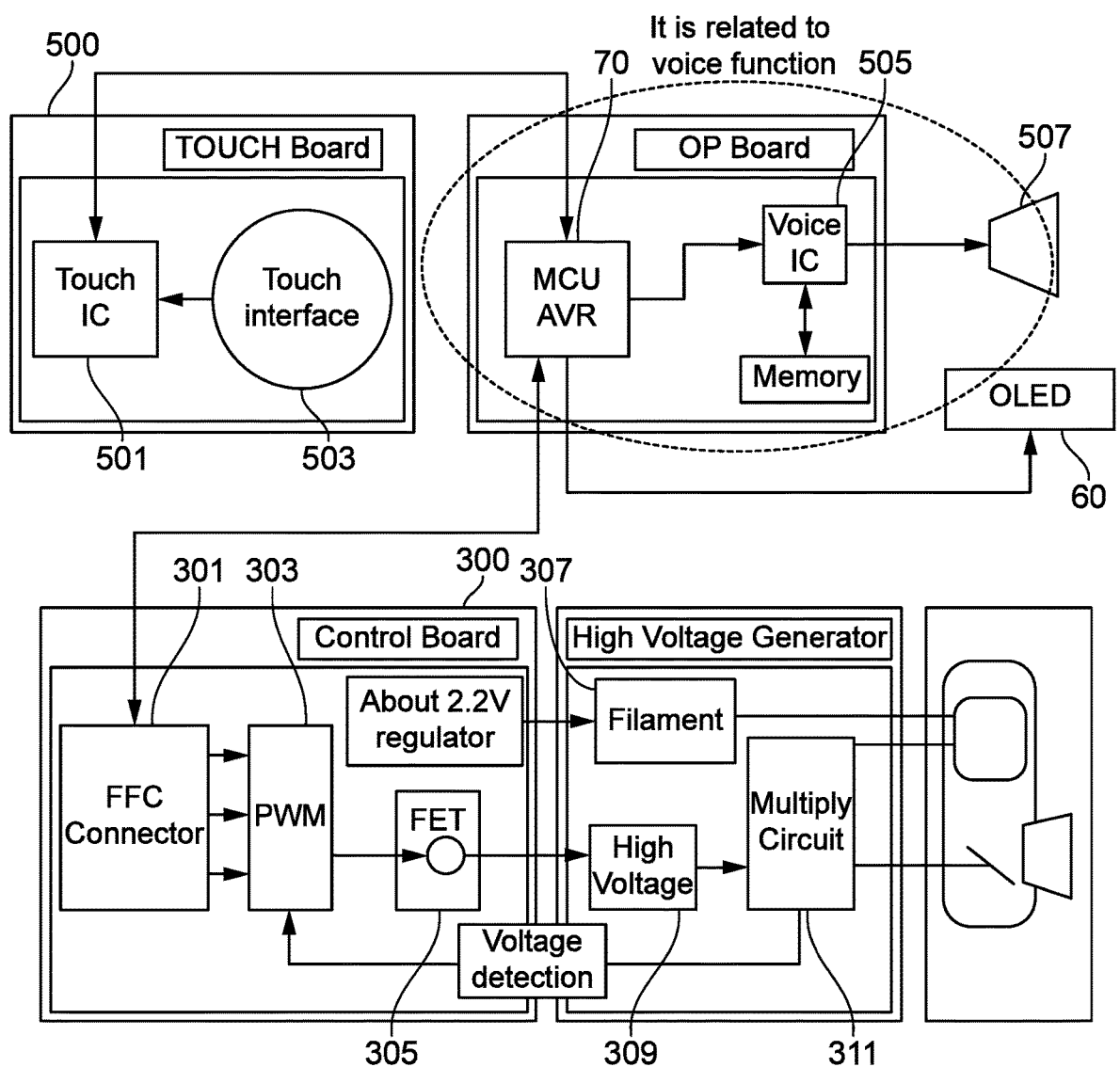
FIG. 7 illustrates a circuit diagram of the x-ray device of the present invention.
Figure 8:
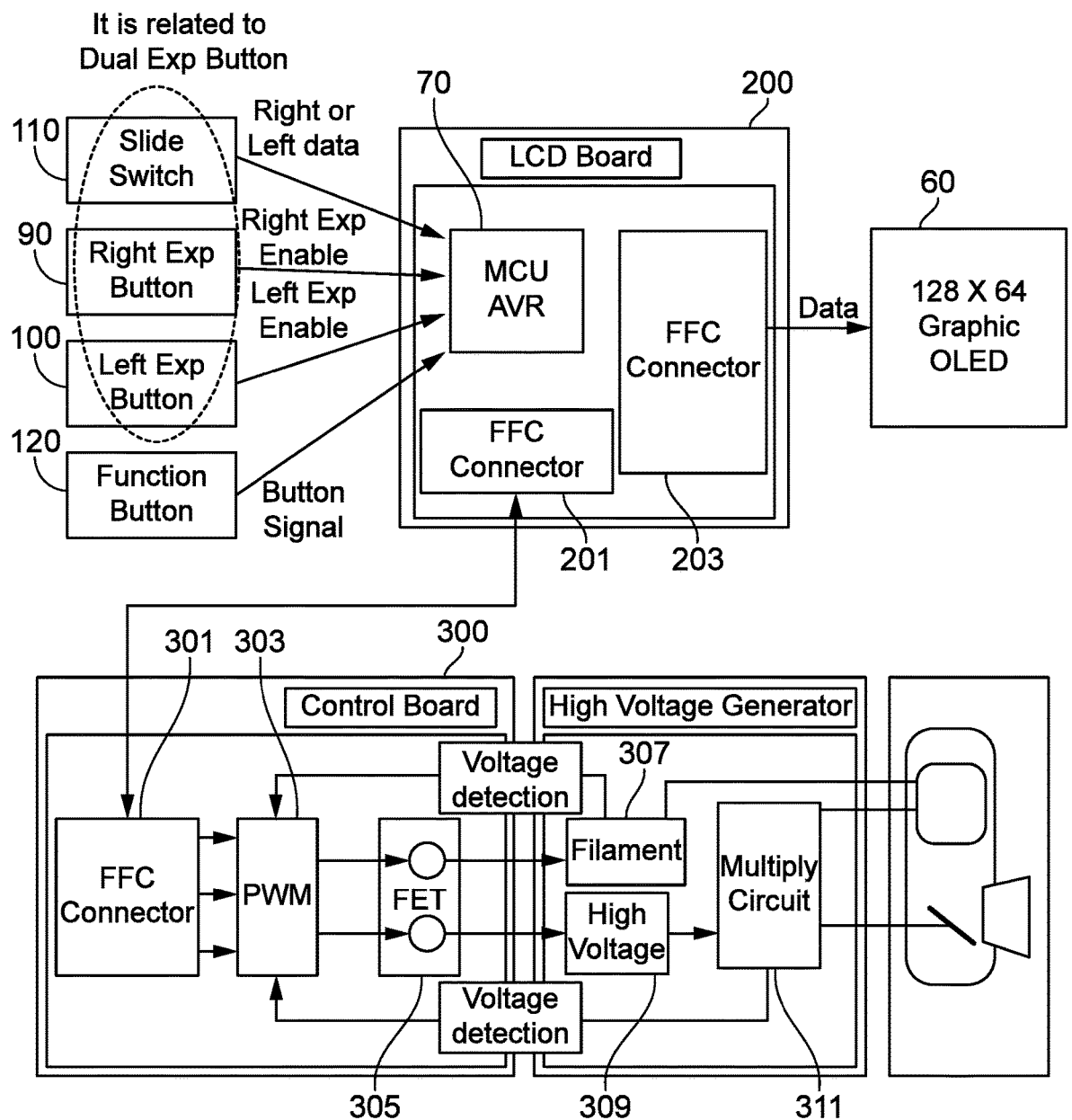
FIG. 8 illustrates another circuit diagram of the x-ray device of the present invention.

FIGS. 7 and 8 illustrates the slide switch 110, the first trigger 90, the second trigger 100 and a function button 120 which selects the particular function required being input to the LCD board 200 (does LCD mean anything) and more particularly to the microcontroller 205. In addition, the control board 300 is connected to the first connector circuit 201 from the third connector circuit 303 positioned on the control board 300. The second connector 203 is connected to a graphic circuit device 400 to display the information on the display screen 60.

The control board 300 may include a pulse width modulated (PWM) circuit 303 to connect to a field effect transistor (FET) circuit 305 which connects to the filament 307 to generate x-rays and a voltage circuit 309 which may be connected to the multiplier circuit 311 to release the x-rays from the x-ray device 10.

Figure 10:
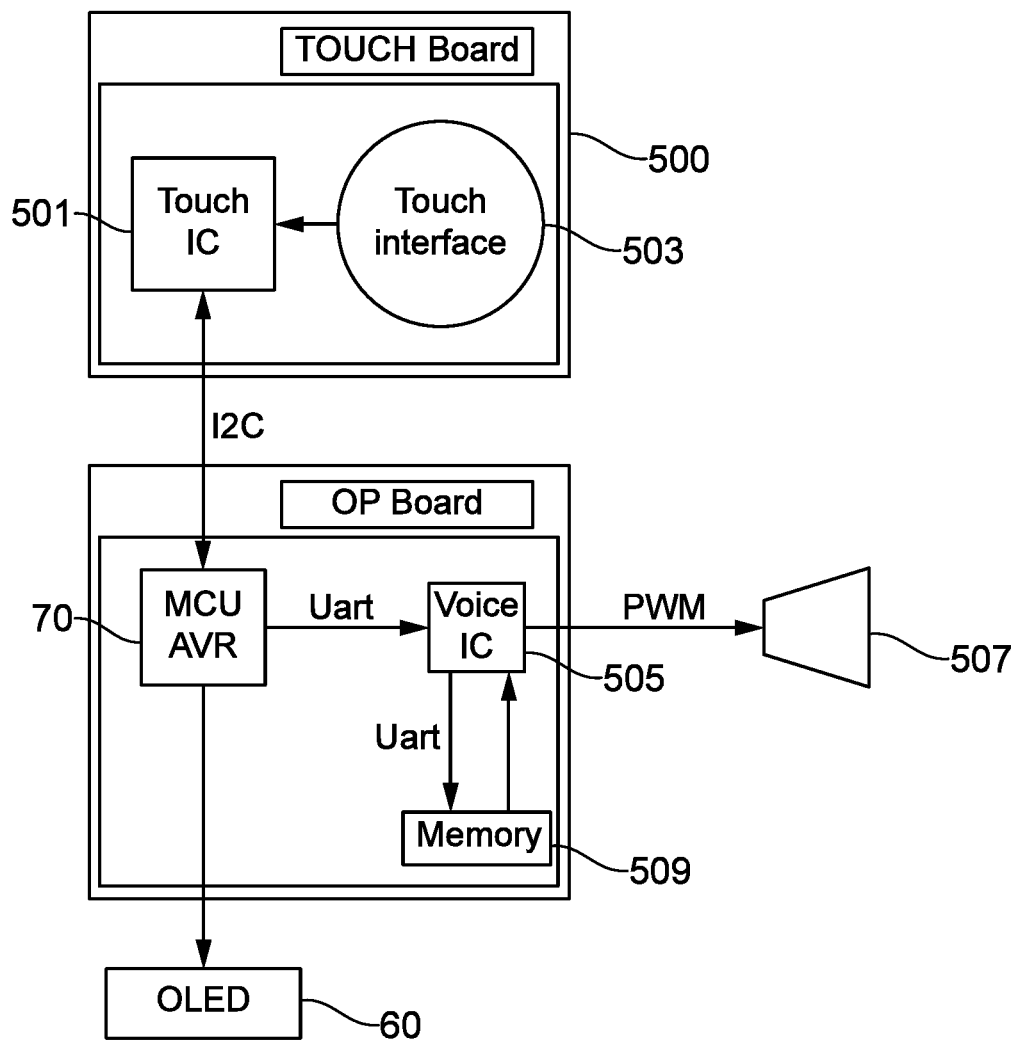
FIG. 10 illustrates another circuit diagram of the x-ray device of the present invention.
Figure 11:
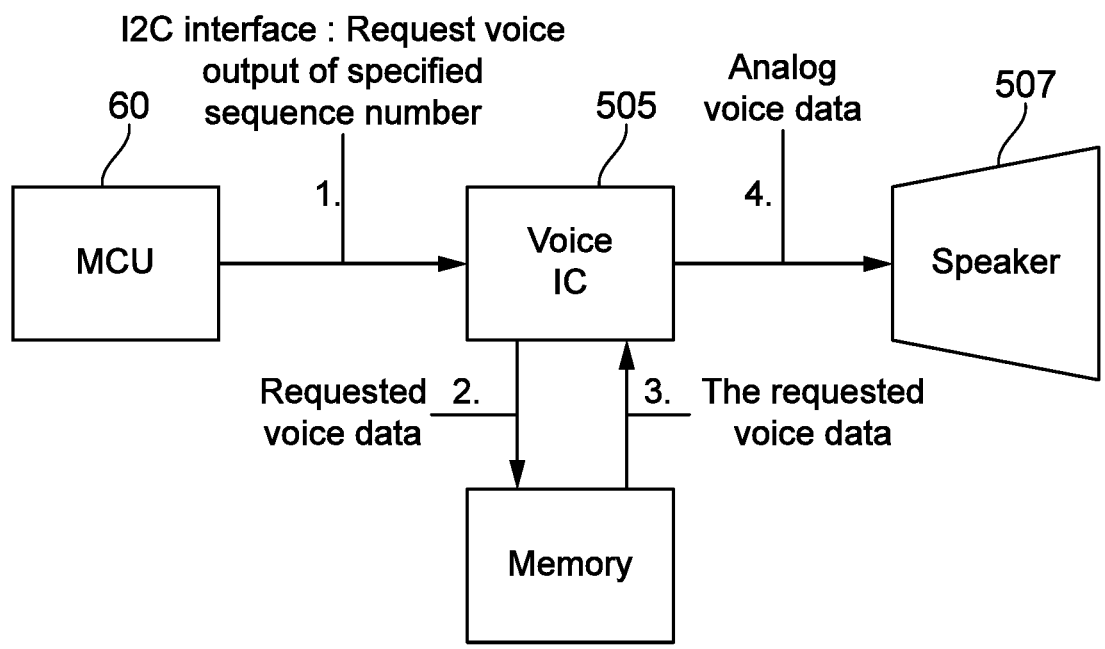
FIG. 11 illustrates another circuit diagram of the x-ray device of the present invention.

FIG. 7, FIG. 10 and FIG. 11 illustrate the touch board 500 which may include a touch interface 501 to generate a signal transmitted to the touch IC 503 when the user touches the touch interface 501, and the signal is transmitted to the controller 70 which may activate the voice IC 505 which may activate the speaker 507; in addition, the controller 70 may activate the display screen 60 and the voice IC 505 may receive voice signals from the memory 509.

Figure 9:
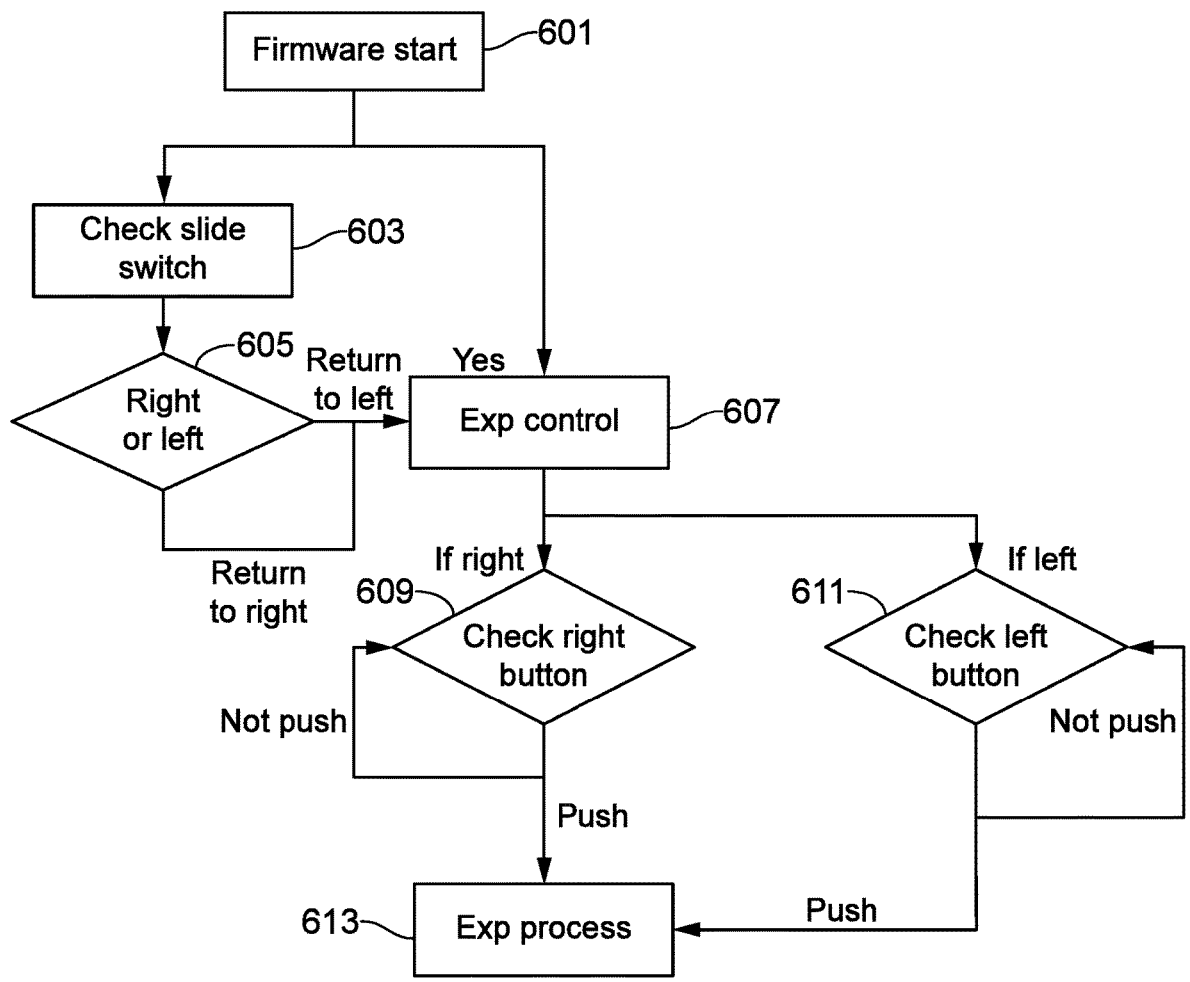
FIG. 9 illustrates a flowchart of the x-ray device of the present invention.

FIG. 9 illustrates the steps to begin the exposure from the x-ray device 10. In step 601, the firmware is initiated and begins. In step 603, the position of the slide switch 110 is determined. In step 605, it is determined if the first trigger 90 is being activated or the second trigger 100 is being activated. In step 607, exposure control is activated. If the slider switch is indicating that the first trigger 90 is to be activated, in step 609, it is determined if the first trigger 90 is actually pushed. If the first trigger 90 is not pushed, then control returns to 609, and if the first trigger 90 has been actually pushed, then the exposure process is executed in step 613. If the second trigger 100 is selected by the slider switch 110 then it is determined if the second trigger switch 100 has that been actually pushed. If the second trigger 100 has not been pushed, then control returns to step 611. If the second trigger 100 has been pushed, then the exposure process is activated in step 613.

Figure 12:
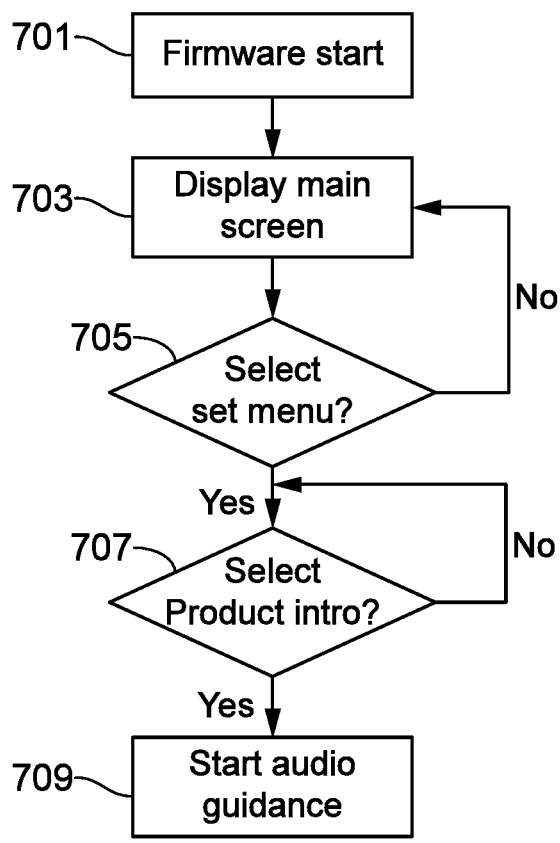
FIG. 12 illustrates a flowchart diagram of the x-ray device of the present invention.
Figure 13:
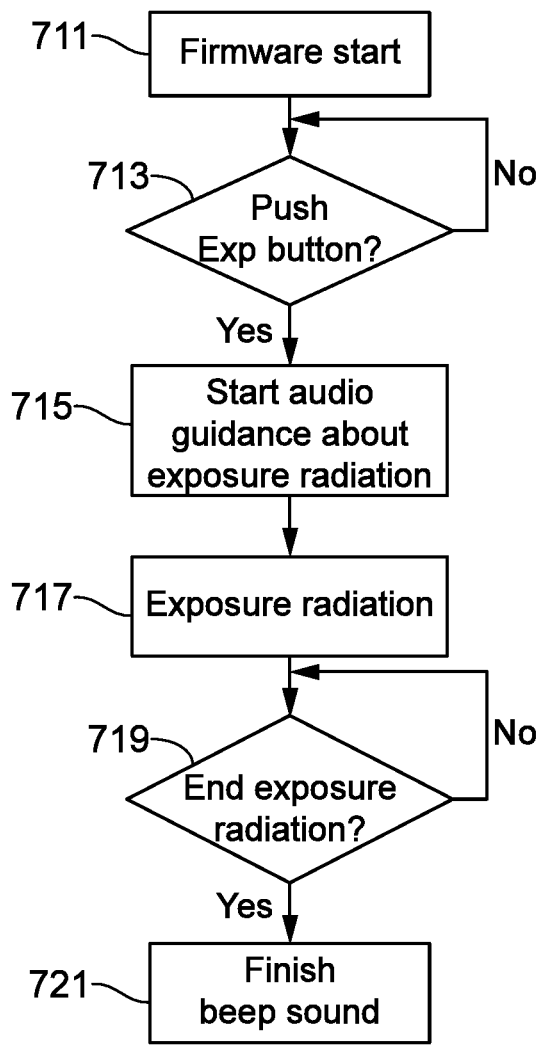
FIG. 13 illustrates another flowchart diagram of the x-ray device of the present invention.

FIGS. 12 and 13 illustrates the steps are associated with the audio guidance of the present invention. In step 701, the firmware is activated, and in step 703 the display screen 60 is activated, and in step 705 it is determined if the select step has been activated from the display screen 60. If the select step has not been activated then control is transferred back to step 703. If the select step has been activated from the display screen 60, in step 707, it is determined if the select product introduction has been selected from the display screen 60. If no, then step 707 is executed until the select product introduction has been selected from the display screen 60. When the select step introduction has been selected, then in step 709, the audio guidance is activated in step 709. In step 711, the firmware is activated. In step 713, it is determined if the exposure button (the first trigger 90 or the second trigger 100) has been pushed by the user. If the exposure button is not been pushed, then step 713 is executed. If the exposure button has been activated, then the audio guidance about exposure to radiation is begun in step 715. In step 717, the x-ray device 10 exposes the target object such as a tooth. In step 719, it is determined if the exposure radiation has been completed. If no, then the step 719 is executed again. If the exposure has ended, in step 721, the audio ends (the beep sound stops).

Figure 14:
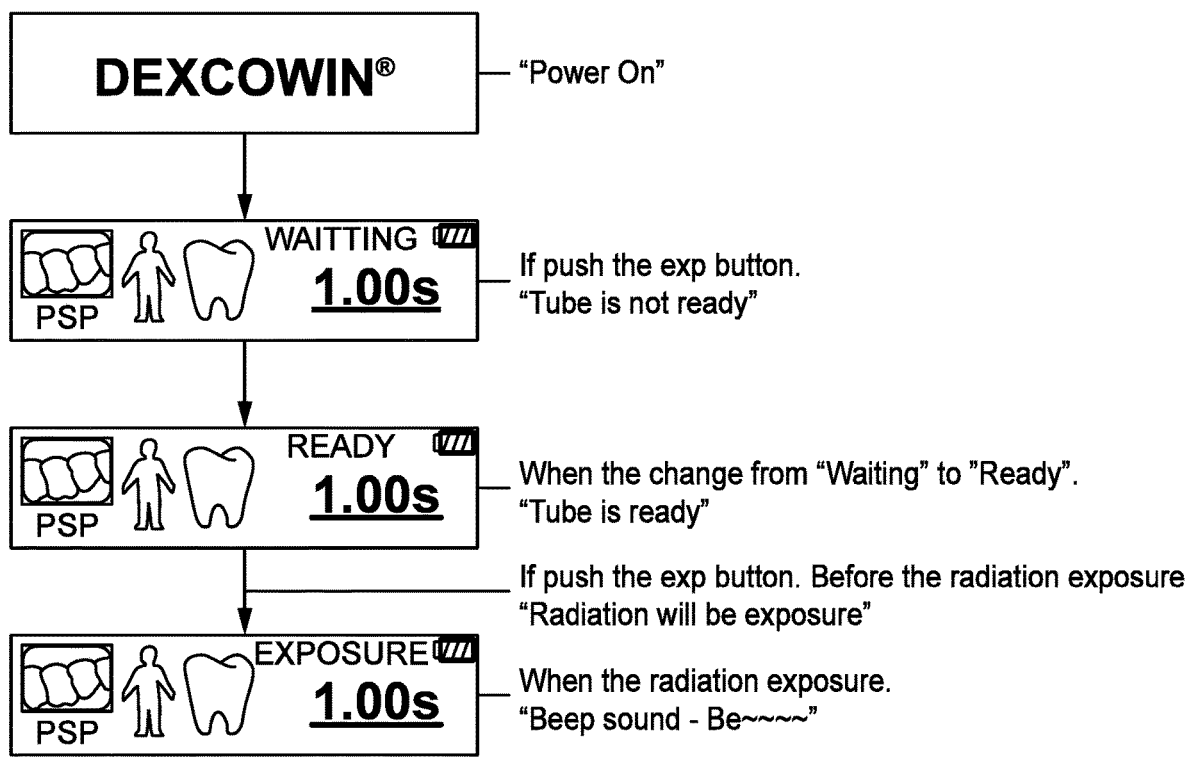
FIG. 14 illustrates a display of the x-ray device of the present invention.

FIG. 14 illustrates a display of the x-ray device of the present invention.

Figure 15:
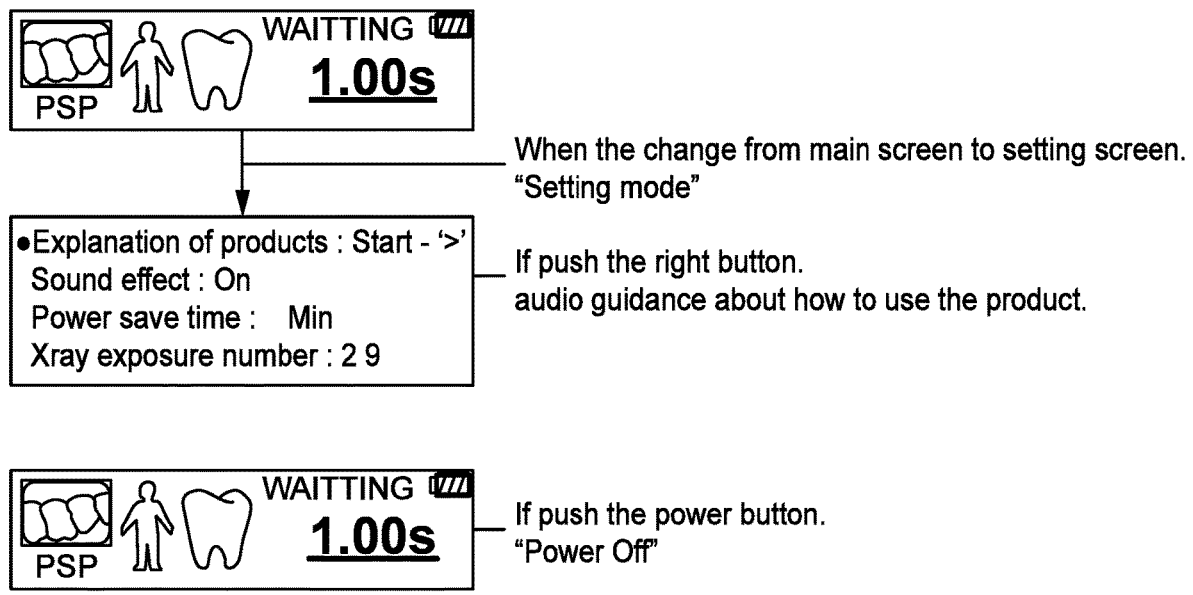
FIG. 15 illustrates another display of the x-ray device of the present invention.

FIG. 15 illustrates another display of the x-ray device of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed.

The invention claimed is:

1. A portable x-ray device for producing x-rays, comprising:
    a housing;
    an exposure device enclosed by the housing to generate x-rays;
    a slide switch connected to the exposure device being movable between a first position and a second position;
    a first trigger to activate the exposure device when the slide switch is in the first position, the first trigger being positioned on a first side of the housing;
    a second trigger to activate the exposure device when the slide switch is in the second position the second trigger being positioned on a second opposed side of the housing.

2. A portable x-ray device for producing x-rays as in claim 1, wherein the x-ray device includes a function button to control the function of the x-ray device.

3. A portable x-ray device for producing x-rays as in claim 1, wherein the x-ray device includes a display screen to display information concerning the exposure.

4. A portable x-ray device for producing x-rays as in claim 3, wherein the x-ray device includes a controller to control the display screen.

5. A portable x-ray device for producing x-rays as in claim 1, wherein the x-ray device includes a sensing circuit.

6. A portable x-ray device for producing x-rays as in claim 1, wherein the x-ray device includes shielding to shield the operator of the x-ray device.

7. A portable x-ray device for producing x-rays as in claim 1, wherein the x-ray device includes a power supply.

\* \* \* \* \*